United States Patent
Kuhn et al.

(10) Patent No.: US 9,328,035 B1
(45) Date of Patent: May 3, 2016

(54) SYSTEMS AND METHODS FOR PRODUCING LIQUID HYDROCARBON FUELS

(71) Applicants: John N. Kuhn, Tampa, FL (US); Babu Joseph, Tampa, FL (US)

(72) Inventors: John N. Kuhn, Tampa, FL (US); Babu Joseph, Tampa, FL (US)

(73) Assignee: University of South Florida, Tampa, FL (US)

( * ) Notice: Subject to any disclaimer, the term of this patent is extended or adjusted under 35 U.S.C. 154(b) by 102 days.

(21) Appl. No.: 14/139,629

(22) Filed: Dec. 23, 2013

Related U.S. Application Data

(60) Provisional application No. 61/748,580, filed on Jan. 3, 2013.

(51) Int. Cl.
C07C 1/04 (2006.01)
C10G 2/00 (2006.01)

(52) U.S. Cl.
CPC ........... *C07C 1/043* (2013.01); *C01B 2203/062* (2013.01); *C01B 2203/10* (2013.01); *C01B 2203/1011* (2013.01); *C01B 2203/82* (2013.01); *C10G 2/33* (2013.01)

(58) Field of Classification Search
CPC ............ C01B 2203/0233; C01B 2203/06; C01B 2203/062; C01B 2203/10; C01B 2203/1005; C01B 2203/1011; C01B 2203/1017; C01B 2203/1023; C01B 2203/1035; C01B 2203/1041; C01B 2203/1047; C01B 2203/1052; C01B 2203/1058; C01B 2203/1064; C01B 2203/1082; C01B 2203/1235; C01B 2203/1241; C01B 2203/82; C07C 1/02; C07C 1/04; C07C 1/041; C07C 1/0425; C07C 1/043; C07C 1/0435; C07C 1/044; C07C 1/0485; C07C 4/02; C07C 4/025; C07C 1/06; C07C 4/06; C07C 2521/00; C07C 2521/04; C07C 2521/06; C07C 2523/00; C07C 2523/04; C07C 2523/10; C07C 2523/38; C07C 2523/40; C07C 2523/46; C07C 2523/54; C07C 2523/70; C07C 2523/745; C07C 2523/74; C07C 2523/755; C07C 2523/76; C10G 2/00; C10G 2/33; C10G 2/331; C10G 2/332; C10G 2/333; C10G 2/34; C10G 2/341; C10G 2/30; C10G 2/32

USPC ......... 502/302, 344, 103, 104, 315, 335, 337, 502/300, 60, 64, 232, 240, 73, 74, 325, 326, 502/338, 415; 422/187, 625

See application file for complete search history.

(56) References Cited

U.S. PATENT DOCUMENTS 5,344,849 A   9/1994 Ayasse
5,621,155 A   4/1997 Benham et al.

(Continued)

OTHER PUBLICATIONS

University of Southern Florida (USF) Division of Patents and Licensing Research Office pdf entitled "One-Step Steam Reforming Plus Fischer-Tropsch Synthesis to Produce Liquid Fuels from Natural Gas" <http://www.research.usf.edu/dpl/content/data/PDF/12B129.pdf>.*

(Continued)

*Primary Examiner* — Jafar Parsa
*Assistant Examiner* — Amy C Bonaparte
(74) *Attorney, Agent, or Firm* — Thomas | Horstemeyer, LLP

(57) ABSTRACT

In one embodiment, liquid hydrocarbon fuels are produced in a single reactor using a hybrid catalyst system including a reforming catalyst, a Fischer-Tropsch synthesis (FTS) catalyst, and a porous material that spatially separates the reforming catalyst from the FTS catalyst.

20 Claims, 3 Drawing Sheets

(56) References Cited

U.S. PATENT DOCUMENTS

| | | |
|---|---|---|
| 6,750,258 B2 | 6/2004 | Wang et al. |
| 6,765,025 B2 | 7/2004 | Ding et al. |
| 6,784,212 B2 | 8/2004 | Steynberg et al. |
| 6,982,287 B2 | 1/2006 | Wang et al. |
| 7,109,248 B2 | 9/2006 | Bowe |
| 7,300,959 B2 | 11/2007 | Vogt et al. |
| 7,468,396 B2 | 12/2008 | Ding et al. |
| 7,829,602 B2 | 11/2010 | Litt et al. |
| 7,943,674 B1 | 5/2011 | Kibby et al. |
| 7,973,086 B1 | 7/2011 | Saxton et al. |
| 8,053,481 B2 | 11/2011 | Ayasse |
| 2014/0128484 A1* | 5/2014 | Hassan ................ C07C 29/153 518/704 |
| 2014/0128485 A1* | 5/2014 | Hassan ................ C07C 2/84 518/704 |

OTHER PUBLICATIONS

Johns ("Combined stream reforming of methane and Fischer-Tropsch synthesis for the formation of hydrocarbons: A proof of concept study" Catalysis Letters, vol. 90, Nos. 3-4, Oct. 2003, p. 187-194).*

ZSM pdf obtained from ACS Material-Advanced Chemical Suppliers < http://www.acsmaterial.com/product.asp?cid=33&id=116>, obtained from the internet on May 28, 2015.*

Yunhua Zhu, et al. "Single-step syngas-to-distillates (S2D) process based on biomass-derived syngas—A techno-economic analysis", Biosource Technology, 117:341-351 (2012).

* cited by examiner

SYSTEMS AND METHODS FOR PRODUCING LIQUID HYDROCARBON FUELS

CROSS-REFERENCE TO RELATED APPLICATION(S)

This application claims priority to U.S. Provisional Application Ser. No. 61/748,580, filed Jan. 3, 2013, which is hereby incorporated by reference herein in its entirety.

BACKGROUND

Natural gas can be converted into liquid hydrocarbon fuels, such as gasoline, jet fuel, diesel, and military fuels. With current methods, two major reactions are used: a first reaction (methane reforming, endothermic, requiring energy or partial oxidation, exothermic, requiring oxygen separation from air) to convert the raw material into synthesis gas or "syngas", and a second reaction (Fisher-Tropsch Synthesis, exothermic, producing energy) to convert the syngas into the fuel.

While such methods are effective, the need for multiple reactors in which those reactions occur add expense to the fuel generation process. In particular, the capital investment costs and energy usage in gas-to-fuel plants are skewed by the need for separate reactors. Energy inefficiencies also arise because the reforming step is endothermic at a high temperature whereas the conversion of syngas into fuel is exothermic at a lower temperature.

In view of the above discussion, it can be appreciated that it would be desirable to have alternative systems and methods for producing liquid hydrocarbon fuels from natural gas.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
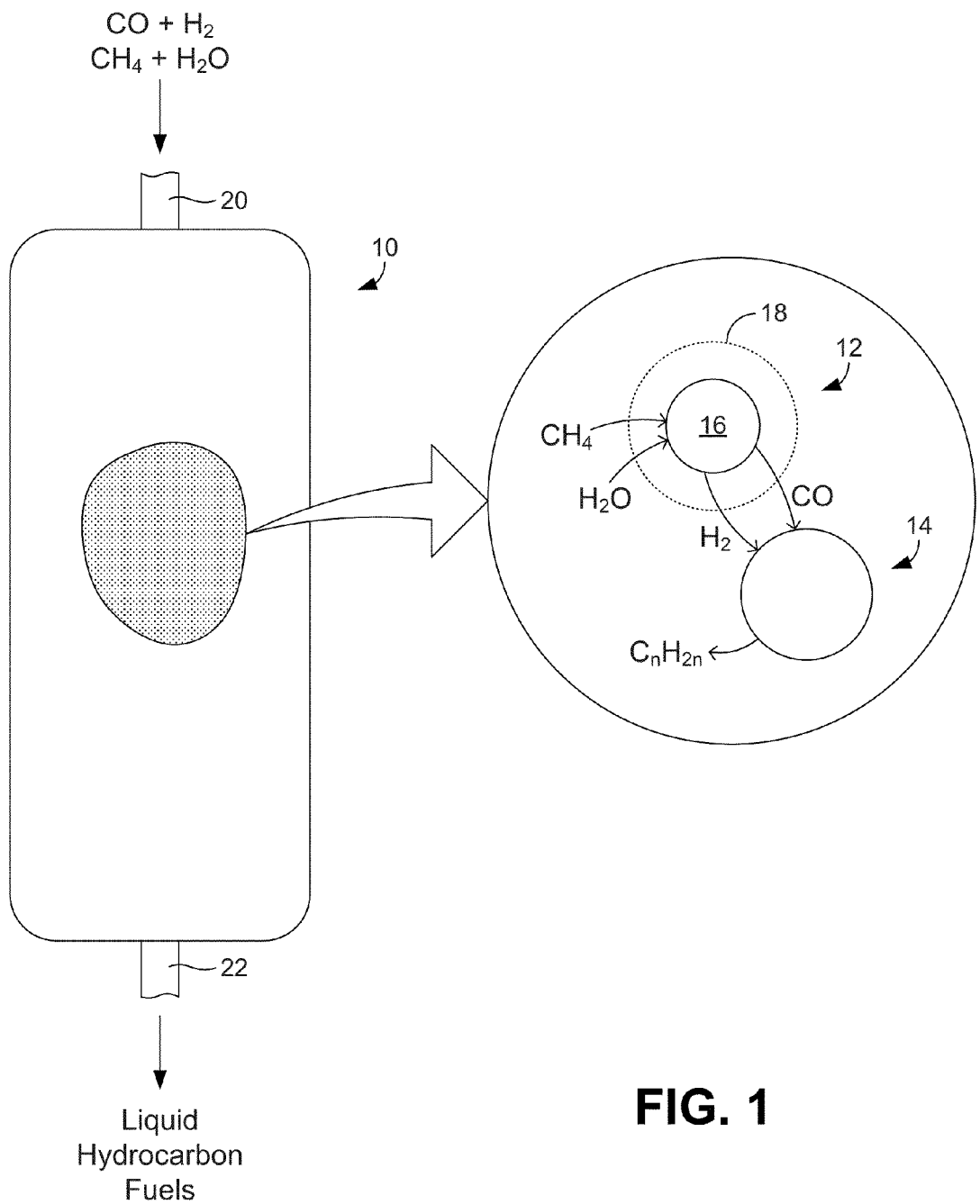
FIG. 1 is a schematic diagram of a first embodiment of a hybrid catalyst system contained within a single reactor.

As described above, it would be desirable to have alternative systems and methods for producing liquid hydrocarbon fuels from natural gas. Disclosed herein are systems and methods for producing liquid hydrocarbon fuels that combine the separate operations of conventional processes to reduce equipment and production costs. More particularly, the systems and methods combine the reforming process and Fischer-Tropsch synthesis (FTS) into a single operation that takes place within a single reactor. In some embodiments, the reactor contains a hybrid catalyst system that includes both a reforming catalyst and an FTS catalyst. The two catalysts are spatially separated by a porous material that enables only certain molecules to pass between the two catalysts.

In the following disclosure, various specific embodiments are described. It is to be understood that those embodiments are example implementations of the disclosed inventions and that alternative embodiments are possible. All such embodiments are intended to fall within the scope of this disclosure.

Disclosed herein is a novel methodology for process intensification by combining multiple catalytic reactions in a single reactor using porous materials to control access to different reaction sites and to overcome thermodynamic and kinetic limitations in order to achieve desired conversion and selectivity. The porous materials have controlled thicknesses and porosities that control transport to different reaction sites of two different catalysts having distinct functions by size-selective transport. This approach is based upon the premise that multifunctional catalysts synthesized with porous coatings can be engineered to control reaction activity, selectivity, and stability, thus combining multiple reaction steps while reducing or eliminating separation steps needed in a process.

A challenge for integrating multiple functions into a single catalytic reactor is the achievement of materials capable of cooperating for multiple functions without a loss in performance in their intended purpose. First, activity and/or selectivity can suffer because of additional species not present during the monofunctional operation of a single reaction. This challenge is observed during partial methane oxidation (thermal intensification replacing endothermic reforming powered by exothermic combustion) to syngas, where combustion products commonly form. These effects of co-mingled reactions and products for different stages have been addressed through the use of membrane reactors. Membrane reactors offer intensification by manipulation of the kinetics and thermodynamics by reactant addition or product removal during the course of the reactions. Second, activity can suffer if catalysts cannot operate under similar temperature, pressure, space velocity, and mixing conditions.

The disclosed invention directly addresses these challenges through the use of porous coatings to control access to different reaction sites and integrated catalyst design to achieve catalysts capable of operating under similar conditions. This approach disrupts the traditional process of designing catalysts for a single reaction and instead focuses the material design on the integration in the process. The use of the engineered catalyst is advantageous over catalytic membrane reactors because it widens the number and types of chemicals possibly employed for intensification. For example, membrane reactors include only applications involving certain species such as hydrogen, oxygen, and carbon. With porous material coatings, a range of molecules becomes possible.

FIG. 1 illustrates an embodiment of a hybrid catalyst system capable of combining endothermic steam reforming with exothermic FTS reactions into a single intensified process to avoid costly energy penalties and mass recycle and alter the economics of gas-to-liquid processes. As mentioned above, the hybrid catalyst system includes both a reforming catalyst and an FTS catalyst that are spatially separated by a metal oxide. As shown in FIG. 1, the hybrid catalyst system is provided within a single reactor 10. The hybrid catalyst system within the reactor 10 includes both reforming catalyst particles 12 and FTS catalyst particles 14. As shown in the detail view of FIG. 1, the reforming catalyst particles 12 comprise a reforming catalyst core 16 that is encapsulated by an porous outer layer or membrane 18. The reforming catalyst within the core 16 can comprise substantially any reforming catalyst. In some embodiments, the reforming catalyst is a relatively low-temperature reforming catalyst to better match the FTS reaction, which tend to be used at relatively lower temperatures. By way of example, the reforming catalyst can comprise a metal catalyst, a metal oxide, rare earth oxides, alkali metals, or a combination thereof. Specific examples include doped Ni/zirconia (YSZ) and mixed perovskite-type oxides, which work at temperatures as low as 350° C. Irrespective of the reforming catalyst that is used, the core 16 can have an outer dimension (e.g., average diameter) of approximately 0.1 to 100 microns (μm).

The outer layer 18 includes many pores that enable small molecules to pass through the layer. In some embodiments, the pores of the outer layer 18 are approximately 0.3 to 1 nanometer (nm) in size (e.g., diameter). In some embodiments, the outer layer 18 is made of a metal oxide, such as a zeolite, silica, titania, zirconia, a metal-organic framework, or ceria. Irrespective of the material, the outer layer 18 can be approximately 5 to 100 nm thick and the reforming catalyst particles 12 can have an outer dimension (e.g., average diameter) of approximately 1 to 100 microns (μm).

The FTS catalyst particles 14 can comprise substantially any FTS catalyst. Example catalysts include a cobalt-based catalyst, an iron-based catalyst, a ruthenium catalyst, each with a possible promoter such as platinum, manganese, magnesium, potassium or similar metals, and combinations thereof. In some embodiments, the FTS catalyst particles 14 comprise an FTS catalyst that is deposited within a support material, such as silica, titania, or alumina. Like the reforming catalyst particles 12, the FTS catalyst particles 14 can have an outer dimension (e.g., average diameter) of approximately 1 to 100 μm.

As depicted in FIG. 1, the hybrid catalyst system preferentially breaks down light hydrocarbons such as methane to hexane while simultaneously promoting the growth of longer chain hydrocarbon synthesis (FTS). In some embodiments, a feedstock of methane ($CH_4$) and water ($H_2O$) is delivered via an inlet 20 into the reactor 10, which can be operated at a temperature of approximately 200 to 500° C. The $CH_4$ and $H_2O$ pass through the outer layer 18 of the reforming catalyst particles 12 and react with the reforming catalyst within the core 16. The $CH_4$ and $H_2O$ then break up or "crack" to form carbon monoxide (CO) and hydrogen ($H_2$), which can then pass through the outer layer 18 so they can react with the FTS catalyst of the particles 14 to produce liquid hydrocarbon fuel.

Figure 2:
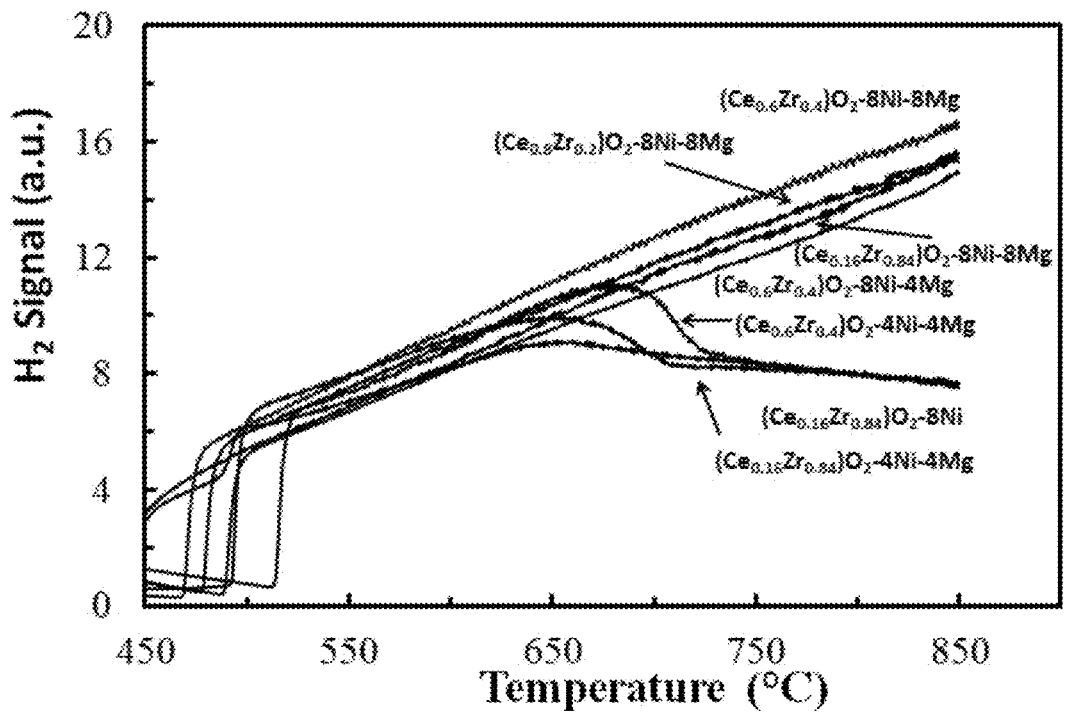
FIG. 2 is a graph that plots hydrogen production from methane, steam, carbon dioxide, and oxygen as a function of temperature over Ni/Mg/(Ce,Zr)$O_2$ catalysts.
Figure 3:
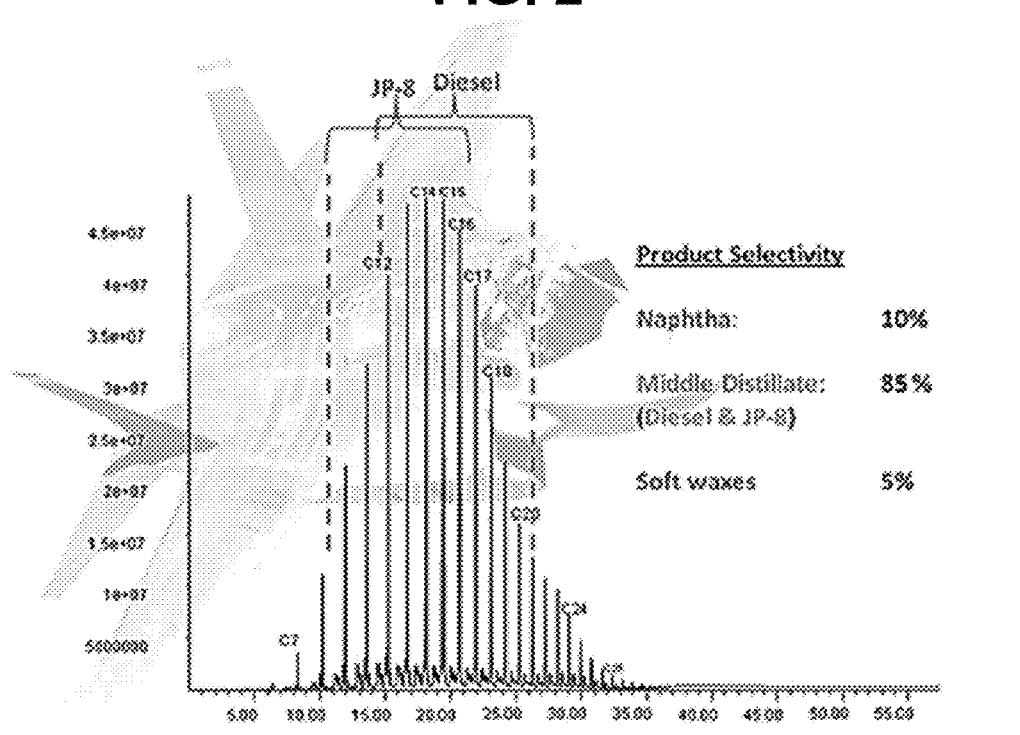
FIG. 3 is a graph that illustrates a hydrocarbon product distribution from various catalysts.

Several low-temperature reforming catalysts were tested that are capable of operating at lower temperatures (e.g., as low as 350° C.). Highlighted in FIG. 2 is an example reforming catalyst that comprised nickel (Ni) ceria-zirconia. This catalyst can, for instance, be combined with high-temperature iron (Fe) FTS catalysts in a single reactor so that both reforming and synthesis can be carried out in parallel. FIG. 3 identifies various FTS catalysts that can be used to produce specific types of fuels.

The hybrid catalyst system described above accomplishes simultaneous exchange of heat and mass with the objective of reducing overall capital and operating costs for the process. The approach is innovative on several levels. First, heat transfer between inter-mixed, dual-bed catalysts provides significant advantages in energy management in the overall process. With the system integrated, the energy produced by the FTS process can be used to drive the exothermic reforming catalysis. Second, with the in-bed conversion of unwanted, lower hydrocarbons back to syngas, the selectivity towards desired hydrocarbons increases. Third, separation and recycle of unwanted products are reduced with the intensified process. Fourth, the process is carried out at a lower temperature, which increases the energy efficiency. It is anticipated that, if a 20% reduction in the cost of the gas-to-liquid conversion can be achieved, the process will be profitable even at oil prices below $80 per barrel.

It is noted that the thickness and the porosity of the porous coating will control the hydrocarbon product distribution from the process. That is, the average molecular weight of the hydrocarbon product will increase with increasing coating thickness and pore diameter. The trend occurs because widening the pore and increasing the diffusion length will force more small hydrocarbons, relative to large ones, into the pathways of conversion back to syngas using the core reforming catalyst. A concentration gradient, caused by the hydrocarbon conversion at the surface of the core catalyst, is a driving force for diffusion into the core. However, the controlled pore size sieves off the hydrocarbons larger than the pore diameter and the pore length limits the transport rate of the hydrocarbons able to enter the pore mouth. Additionally, thermal gradients may influence the mass transfer driving forces and rates. It is also likely that the outer layer material (e.g., zeolite) will catalyze cracking of hydrocarbons that enter the pores, which would make the average hydrocarbon size non-linear as a function of the pore diameter and pore length. This phenomenon will disrupt the traditional Anderson-Schulz-Flory (ASF) product distribution from the process.

It is further noted that the combined processes may also lead to improved thermal management. The balancing of the reactions' enthalpies for the endothermic reforming reaction and the exothermic chain growth reaction will permit heat integration by decreasing the need to supply heat to the reforming, remove heat from the CO hydrogenation reactor, and provide energy for the separation.

Figure 4:
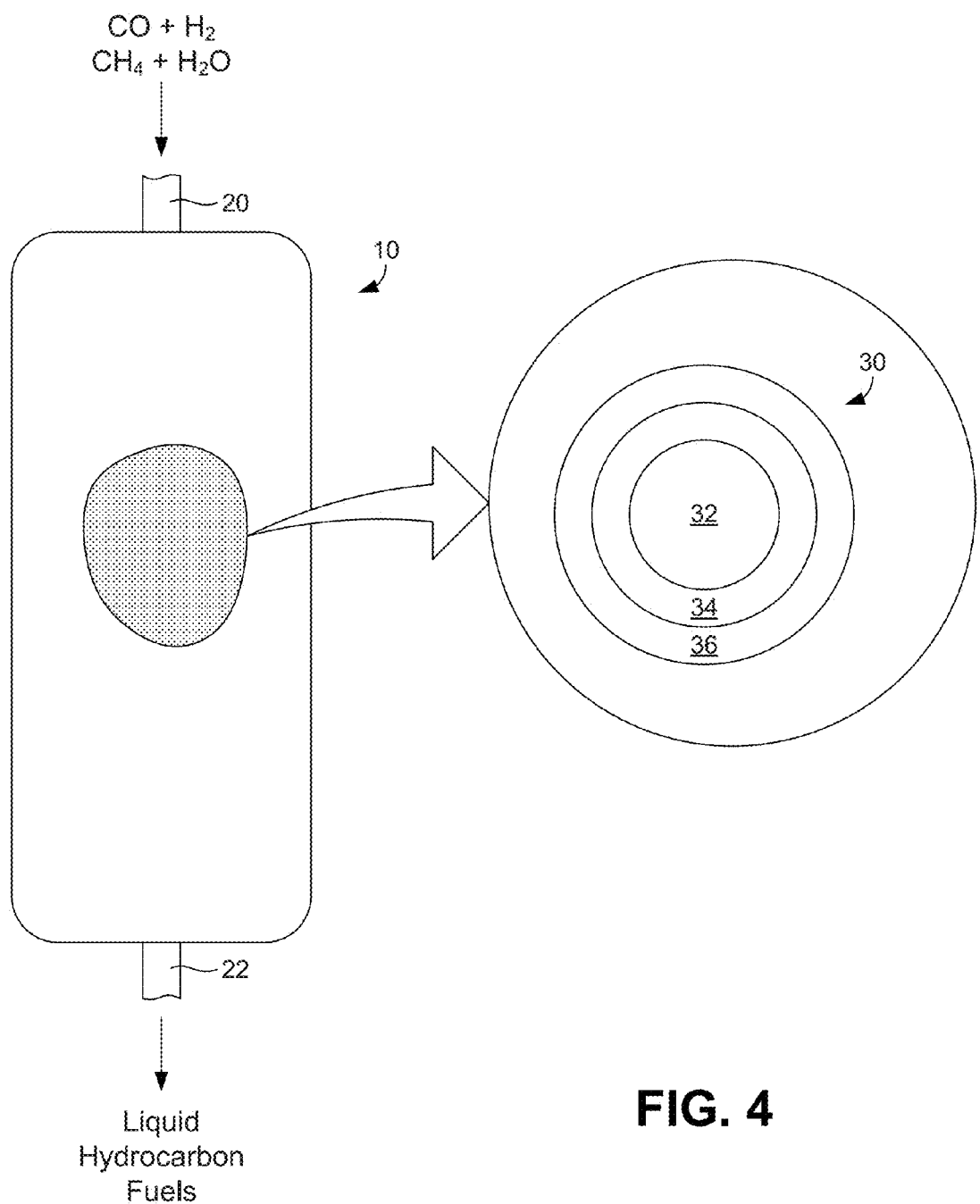
FIG. 4 is a schematic diagram of a second embodiment of a hybrid catalyst system contained within a single reactor.

There are other ways of spatially separating the reforming catalyst and the FTS catalyst. FIG. 4 illustrates a second embodiment for a hybrid catalyst system that uses a single reactor 10. As is shown in that figure, the hybrid catalyst system includes hybrid catalyst particles 30 that, similar to the particles 12, comprise a reforming catalyst core 32 that is encapsulated by a porous outer layer 34 or membrane (e.g., metal oxide). In this embodiment, however, the outer layer 34 is coated with an FTS catalyst layer 36. The reforming catalyst, metal oxide, and FTS catalyst used to form the core 32, layer 34, and layer 36, respectively, can each be selected from the examples described above in relation to FIG. 1.

While the above discussion has focused on the conversion of natural gas into liquid hydrocarbon fuels, it is noted that similar one-step processes could be used in other applications. For example, a similar process can be used to convert biomass, coal, and short-chain alcohol feedstocks into liquid hydrocarbon fuel. More generally, the disclosed approach provides general platform for integration of multiple processes, which could involving reactants, products, and poisons of different sizes into a single operation. The methodology is therefore relevant to many processes, including methanol poisoning in fuel cells reactions and poisoning in biomass and petroleum processing.

The invention claimed is:

1. A hybrid catalyst system for producing liquid hydrocarbon fuels in a single reactor, the system comprising:
   a reforming catalyst;
   a Fischer-Tropsch synthesis (FTS) catalyst; and
   a porous material that spatially separates the reforming catalyst from the FTS catalyst such that fluids can only pass between the catalysts by passing through the porous material.

2. The hybrid catalyst system of claim 1, wherein the reforming catalyst is a low-temperature catalyst that can be used to crack methane with the aid of an oxidant at a temperature of approximately 200 to 550° C.

3. The hybrid catalyst system of claim 1, wherein the reforming catalyst is selected from the group consisting of nickel catalyst, metal catalyst, a metal oxide, rare earth oxides, alkali metals, and combinations thereof.

4. The hybrid catalyst system of claim 1, wherein the porous material has pores that are approximately 0.3 to 1 nanometers in size.

5. The hybrid catalyst system of claim 1, wherein the porous material comprises a metal oxide.

6. The hybrid catalyst system of claim 5, wherein the metal oxide is selected from the group consisting of zeolites, metal oxides, silica, ceria, zirconia, titania, metal-organic frameworks, and combinations thereof.

7. The hybrid catalyst system of claim 1, wherein the reforming catalyst and the porous material are combined to form catalyst particles that include a reforming catalyst core encapsulated by a layer of the porous material.

8. The hybrid catalyst system of claim 7, wherein the layer of porous material is approximately 5 to 100 nanometers thick.

9. The hybrid catalyst system of claim 7, wherein the reforming catalyst particles have an outer dimension of approximately 1 to 100 microns.

10. The hybrid catalyst system of claim 7, wherein the FTS catalyst is contained in a layer that covers the layer of porous material.

11. The hybrid catalyst system of claim 1, wherein the FTS catalyst is selected from the group consisting of iron-based catalyst, cobalt-based catalyst, ruthenium-based catalyst, and combinations thereof.

12. The hybrid catalyst system of claim 1, wherein the FTS catalyst comprises FTS catalyst that is deposited within a support material.

13. The hybrid catalyst system of claim 12, wherein the support material comprises silica or alumina.

14. A system for producing liquid hydrocarbon fuels, the system comprising:

a reactor adapted to receive methane and water and output liquid hydrocarbon fuels; and a hybrid catalyst provided within the reactor, the hybrid catalyst including a reforming catalyst, a Fischer-Tropsch synthesis (FTS) catalyst, and a porous material that spatially separates the reforming catalyst from the FTS catalyst such that fluids can only pass between the reforming catalyst and the FTS catalyst by passing through the porous material.

15. The system of claim 14, wherein the hybrid catalyst comprises catalyst particles that include a reforming catalyst core encapsulated by the porous material.

16. The system of claim 15, wherein the FTS catalyst covers the porous material of the particles.

17. The system of claim 14, wherein the porous material comprises a metal oxide.

18. A method for producing liquid hydrocarbon fuels, the method comprising:

providing a hybrid catalyst including a reforming catalyst and a Fischer-Tropsch synthesis (FTS) catalyst within a single reactor, the two catalysts being spatially separated by a porous material such that fluids can only pass between the catalysts by passing through the porous material;

heating the reactor to a temperature of approximately 200 to 550° C.; and delivering methane and water to the reactor as feedstock that will be reformed and synthesized to produce liquid hydrocarbon fuel.

19. The method of claim 18, wherein the hybrid catalyst comprises catalyst particles that include a reforming catalyst core that is encapsulated by the porous material.

20. The method of claim 19, wherein the FTS catalyst covers the porous material of the particles.

* * * * *